(12) United States Patent
Cook et al.

(10) Patent No.: US 6,696,298 B2
(45) Date of Patent: Feb. 24, 2004

(54) MULTI-CHANNEL REAGENT DISPENSING APPARATUS

(75) Inventors: Ronald M. Cook, Novato, CA (US); Rand Dill, Corte Madera, CA (US); Arnie Baltzley, San Anselmo, CA (US)

(73) Assignee: Biosearch Technologies, Inc., Novato, CA (US)

( * ) Notice: Subject to any disclaimer, the term of this patent is extended or adjusted under 35 U.S.C. 154(b) by 0 days.

(21) Appl. No.: 10/012,729

(22) Filed: Dec. 7, 2001

(65) Prior Publication Data

US 2003/0109060 A1 Jun. 12, 2003

(51) Int. Cl.[7] .................................................. G01N 1/10
(52) U.S. Cl. .............................. 436/54; 436/43; 436/48; 436/180; 422/100; 422/151; 73/863.31; 222/145.3
(58) Field of Search ........................ 422/99, 100, 102, 422/104, 151, 130; 436/180, 43, 48, 49, 54; 73/863.31; 222/145.3

(56) References Cited

U.S. PATENT DOCUMENTS

| | | | |
|---|---|---|---|
| 4,964,539 A | * 10/1990 | Mueller | 222/94 |
| 5,814,700 A | 9/1998 | Brennan | |
| 5,837,858 A | 11/1998 | Brennan | |
| 6,001,311 A | 12/1999 | Brennan | |
| 6,069,243 A | 5/2000 | Scozzari | |
| 6,166,198 A | 12/2000 | Livingston | |

* cited by examiner

Primary Examiner—Lyle A. Alexander
(74) Attorney, Agent, or Firm—Townsend and Townsend and Crew LLP (57) ABSTRACT

Embodiments of the present invention are directed to an improved chemical synthesis apparatus for performing chemical synthesis such as nuclei acid synthesis in a plurality of reaction wells or cells in an efficient manner. The apparatus employs dispenser heads that each include a cluster of nozzles which are fluidically coupled to a plurality of reagent sources for dispensing different reagents through the single dispenser head. Because each dispenser head is capable of dispensing a plurality of different reagents, the apparatus can perform simultaneous synthesis in a plurality of cells at a high throughput without complex and elaborate control of movement of the dispenser heads relative to the cells.

28 Claims, 8 Drawing Sheets

MULTI-CHANNEL REAGENT DISPENSING APPARATUS

BACKGROUND OF THE INVENTION

The present invention relates generally to solid phase processing and, more particularly, to an apparatus for dispensing reagents and other fluids to a plurality of reaction sites for solid phase processing including solid phase synthesis of complex chemicals such as oligonucleotides and the like.

A variety of separative, synthetic, and enzymatic or otherwise catalytic processes use beds of particulate material with transport of reactants, reagents and products or eluants in solution through the bed. In addition, many reactions are known in which the products are separated by concentration in one of two or more phases. These processes include, among others, ion exchange chromatography, gel filtration, ion exclusion chromatography, affinity chromatography, separations based on hydrophobicity, purification based on hybridization, peptide synthesis, oligonucleotide synthesis, and polysaccharide synthesis including combinations of the last three. These processes may be carried out on a small scale for analytical purposes or process design, and are then often scaled up for preparative work. In nearly all examples the solid phase particulates are packed in a closed column with a porous frit on the lower end, an optional frit at the top, and with fluid-connections at both ends so that liquid can flow in either direction through the bed. To achieve efficiency and high resolution with solid phase supports, all volume elements of all fluids should flow through paths of identical composition and nearly identical length, and all particles in the bed should be exposed to the same succession of liquids under the same conditions.

In solid phase systems, some interaction occurs between the solutes running through the bed and the particles composing the bed. This interaction may be based on secondary forces (ionic, hydrophobic, or on immunochemical interactions, or base pairing) or primary valencies as when amino acids or nucleotides are added to a growing chain on the solid phase support, or when immobilized enzymes cleave substrates flowing through the bed, or when enzymes in solution react with substrates attached to the packing. In addition, solvents or reagents of successively differing composition which dissociate adsorbed or otherwise attached bound molecular species, or which cleave off protective groups, or compounds including polymers which have been synthesized on the support may be made to flow through the support. The dissociated or cleaved substances then are free to flow out of the bed in flowing liquid.

In particular, nucleic acid synthesis (generally referred to as "DNA synthesis") is the process of constructing synthetic single-stranded oligonucleotide through linking of nucleotide, the basic building blocks for DNA. In an automated system, the various steps are carried out by a reagent delivery system which dispenses a number of chemical reagents in a predetermined sequence in a cycle into a synthesis reaction column containing the solid-phase support, according to instructions from the system controller or computer. After the desired number of cycles have been completed, the synthesized oligonucleotide is separated from the reaction column and collected in a vial. This step is generally referred to as "cleavage". The oligonucleotide may further be subject to a step generally referred to as "deprotection" to complete isolation of the oligonucleotide. In a process for synthesizing polynucleotides on a solid support, the solid support traditionally consists of glass beads of controlled porosity (CPG) or, more generally, of particles of a functionalized inorganic or organic polymer.

The isolation of oligonucleotide involves the treatment of the solid bound oligonucleotide with a cleavage and/or deprotection reagent. Typically, this reagent is concentrated ammonia solution in water but can be other homogeneous or heterogeneous solutions of appropriate bases, alcohols and water. The cleavage and deprotection process is typically performed in two steps. The cleavage of the oligonucleotide is performed at room temperature for approximately one hour before decanting the mixture into a pressure-sealable vessel for extended higher temperature treatment to effect the removal of secondary protecting groups on the synthetic oligonucleotide. This two step process reduces the quantity of support related contaminants in the final isolated product.

The use of a single nozzle for delivering different reagents into a reaction site, well, or column is not feasible because the nozzle will need to be cleaned or flushed out between reagents to avoid contamination, resulting in a high cost and a low throughput. In one conventional chemical synthesis system, a plurality of reagent dispensing nozzles are arranged in a linear array, and the plate containing the reaction cell(s) or column(s) is moved under the linear array to receive reagents from the dispensing nozzles one at a time. The throughput remains low.

Another synthesis apparatus is disclosed in U.S. Pat. Nos. 5,814,700, 5,837,858, and 6,001,311 employing an array of nozzles. A transport mechanism aligns the reaction wells and selected nozzles for deposition of the liquid reagent into the selected reaction wells. Elaborate manipulation of the transport mechanism is used to dispense reagents from the various nozzles into the various reaction wells in sequence to provide simultaneous synthesis in the reaction wells. The throughput is still relatively low because each nozzle can dispense only one reagent.

BRIEF SUMMARY OF THE INVENTION

Embodiments of the present invention are directed to an improved chemical synthesis apparatus for performing chemical synthesis such as nuclei acid synthesis in a plurality of reaction wells or cells in an efficient manner. The apparatus employs dispenser heads that each include a cluster of nozzles which are fluidically coupled to a plurality of reagent sources for dispensing different reagents through the single dispenser head. Because each dispenser head is capable of dispensing a plurality of different reagents, the apparatus can perform simultaneous synthesis in a plurality of cells at a high throughput without complex and elaborate control of movement of the dispenser heads relative to the cells.

In accordance with an aspect of the present invention, a multi-channel reagent dispenser head for introducing a plurality of reagents into a reaction site comprises a dispenser head body having a dispensing end which is configured to dispense a plurality of reagents from a plurality of reagent sources. A group of nozzles include a plurality of reagent dispensing nozzles which are fluidically coupled with the plurality of reagent sources. The group of nozzles are clustered to provide a plurality of nozzle outlets in the dispenser head body to introduce reagents from the plurality of reagent sources through the dispensing end of the dispenser head body into the reaction site.

In some embodiments, the plurality of reagent dispensing nozzles are each separately coupled with one of the plurality of reagent sources. The plurality of reagent dispensing nozzles may be separately coupled with reagent sources of building block elements such as bases A, C, G, T, and an activator such as tetrazole. Alternatively, the plurality of reagent dispensing nozzles may be separately coupled with reagent sources of acid deblock, oxidizers, and capping agents. The group of nozzles desirably include a wash nozzle which is fluidicly coupled with a source of wash solvent. The wash solvent may comprise acetonitrile. The group of nozzles desirably include a vacuum nozzle which is coupled to a vacuum source. The nozzle outlet of the vacuum nozzle may be disposed proximal of the nozzle outlets of the reagent dispensing nozzles. In specific embodiments, the dispensing end of the dispenser head body has a maximum dimension of about 9 mm. The nozzles each have an outer diameter of less than about $1/16$ inch.

In accordance with another aspect of the present invention, a multi-channel reagent dispenser apparatus for introducing a plurality of reagents into a plurality of reaction sites comprises a plurality of reagent sources, and a plurality of reagent dispensing nozzles each coupled with one of the plurality of reagent sources. A plurality of dispenser heads each include a dispenser head body having a dispensing end which is configured to dispense a plurality of reagents from the plurality of reagent sources. Each dispenser head body has therein a group of nozzles being clustered to provide a plurality of nozzle outlets in the dispenser head body to introduce reagents from the plurality of reagent sources through the dispensing end of the dispenser head body into one of the reaction sites. The group of nozzles include more than one reagent dispensing nozzle from the plurality of reagent dispensing nozzles.

In some embodiments, a plurality of reagent dispensing nozzle valves are each coupled with one of the reagent dispensing nozzles to control reagent flow from the reagent sources to the reagent dispensing nozzles. At least one wash nozzle is coupled with at least one source of wash solvent. The group of nozzles clustered in each dispenser head body include at least one wash nozzle. At least one wash nozzle valve is each coupled with one of the at least one wash nozzle to control wash solvent flow from the at least one source of wash solvent to the at least one wash nozzle. The group of nozzles clustered in each dispenser head body include a vacuum nozzle which is coupled to a vacuum source. A vacuum nozzle valve is coupled with the vacuum nozzle to control vacuum flow through the vacuum nozzle.

In some embodiments, the plurality of dispenser heads comprise at least one first dispenser head and at least one second dispenser head. Each first dispenser head has therein a cluster of first nozzles being coupled with a first set of the plurality of reagent sources. Each second dispenser head has therein a cluster of second nozzles being coupled with a second set of the plurality of reagent sources which are different from the first set of reagent sources. The first set of reagent sources may comprise building block elements such as bases A, C, G, T, and an activator such as tetrazole. The second set of reagent sources may comprise acid deblock, oxidizers, and capping agents. A first actuator is configured to move each of the at least one first dispenser head from one reaction site to another reaction site to introduce reagents from the first set of reagent sources into the reaction sites. A second actuator is configured to move each of the at least one second dispenser head from one reaction site to another reaction site to introduce reagents from the second set of reagent sources into the reaction sites. A controller is coupled with the first and second actuators to automatically control movements of the at least one first dispenser head and the at least one second dispenser head to introduce reagents from the first and second sets of reagent sources separately into the reaction sites.

In specific embodiments, a plurality of reagent dispensing nozzle valves are each coupled with one of the reagent dispensing nozzles. The controller is coupled with the reagent dispensing nozzle valves to control reagent flow from the reagent sources to the first nozzles in the at least one first dispenser head and to the second nozzles in the at least one second dispenser head. The dispensing end of each dispenser head body has a maximum dimension of about 9 mm. The plurality of dispenser heads comprise a plurality of first dispenser heads and a plurality of second dispenser heads. The first dispenser heads are spaced about 9 mm apart, and the second dispenser heads are spaced about 9 mm apart.

The plurality of reagent sources each are delivered to the reagent dispensing nozzles by pressurization with an inert gas. The reaction sites are evacuated under vacuum assist. The reaction sites are disposed in an array provided in a plurality of vacuum trays which are formed on a single block. The apparatus is disposed in an inert environment, such as nitrogen or argon.

In accordance with another aspect of the present invention, a method for introducing a plurality of reagents into a plurality of reaction sites comprises providing a plurality of reagent sources, a plurality of reagent dispensing nozzles each coupled with one of the plurality of reagent sources, and a plurality of dispenser heads. Each dispenser head includes a dispenser head body having a dispensing end. Each dispenser head body has therein a group of nozzles being clustered to provide a plurality of nozzle outlets in the dispenser head body. The group of nozzles include more than one reagent dispensing nozzle from the plurality of reagent dispensing nozzles. The method further comprises controlling flows of reagents from the plurality of reagent sources through the plurality of reagent dispensing nozzles to dispense a plurality of reagents via the group of nozzles clustered in each dispenser head body through the dispensing end of the dispenser head body into one of the reaction sites.

In some embodiments, the flows of reagents through each dispenser head body are controlled by operating a plurality of reagent dispensing valves each coupled with one of the reagent dispensing nozzles based on flow rates to dispense preset amounts of reagents via the group of nozzles clustered in each dispenser head body at preset times through the dispensing end of the dispenser head body into one of the reaction sites. The flows of reagents through each dispenser head body are controlled to provide one reagent at a time through the dispenser head body.

The method may further comprise providing at least one source of wash solvent and at least one wash nozzle coupled with the at least one source of wash solvent, wherein the group of nozzles clustered in each dispenser head body include at least one wash nozzle. The wash solvent is dispensed through the at least one wash nozzle in each dispenser head body at preset times. The method may further comprise providing a vacuum nozzle in the group of nozzles clustered in each dispenser head body, and drawing a vacuum through the vacuum nozzle in each dispenser head body between dispensing different reagents through the dispenser head body.

In some embodiments, the plurality of dispenser heads comprise at least one first dispenser head and at least one second dispenser head. Each first dispenser head has therein a cluster of first nozzles being coupled with a first set of the plurality of reagent sources. Each second dispenser head has therein a cluster of second nozzles being coupled with a second set of the plurality of reagent sources which are different from the first set of reagent sources. The method further comprises moving each of the at least one first dispenser head from one reaction site to another reaction site to introduce reagents from the first set of reagent sources into the reaction sites. The method may further comprise moving each of the at least one second dispenser head from one reaction site to another reaction site to introduce reagents from the second set of reagent sources into the reaction sites. The at least one first dispenser head and the at least one second dispenser head are moved automatically by computer control.

In specific embodiments, the plurality of dispenser heads comprise a plurality of first dispenser heads, and flows through the first nozzles in the first dispenser heads are controlled to dispense reagents from the first set of reagent sources to separate reaction sites simultaneously. The plurality of dispenser heads comprise a plurality of second dispenser heads, and flows through the second nozzles in the second dispenser heads are controlled to dispense reagents from the second set of reagent sources to separate reaction sites simultaneously.

DESCRIPTION OF THE SPECIFIC EMBODIMENTS

The present invention is directed to a multi-channel reagent dispensing system for nuclei acid synthesis or the like. One embodiment of a reagent dispensing system 10 is shown in the simplified schematic diagram of FIG. 1. The reagent dispensing system 10 includes a plurality of reagent and wash solvent sources 12 which are fluidicly coupled with a plurality of dispenser heads 14 to supply solution phase reagents and wash solvents to the dispenser heads. In the embodiment shown, the dispensing system 10 includes two sets of dispenser heads 14a, 14b, which are fluidicly coupled with two sets of reagent and wash solvent sources or other fluid sources 12a, 12b. The first set of dispenser heads 14a are arranged on a first carrier or support 15a which is driven by a first actuator 18a, while the second set of dispenser heads 14b are arranged on a second carrier or support 15b which is driven by a second actuator 18b. A controller 20 may be provided to automatically control the actuators 18a, 18b.

A plurality of vacuum plates or trays 22 are provided, and each vacuum plate 22 supports a plurality of cells or columns or reactors 24 which are evacuated under vacuum assist by a vacuum source coupled to an opening in each vacuum plate 22. In some embodiments, separate vacuum plates 22 are placed together. In the embodiment shown in FIG. 1, the vacuum plates 22 are formed on a single body 26, for instance, by milling them out of a plastic block. This can save space and improve throughput by providing vacuum plates 22 that are close together.

Figure 1:
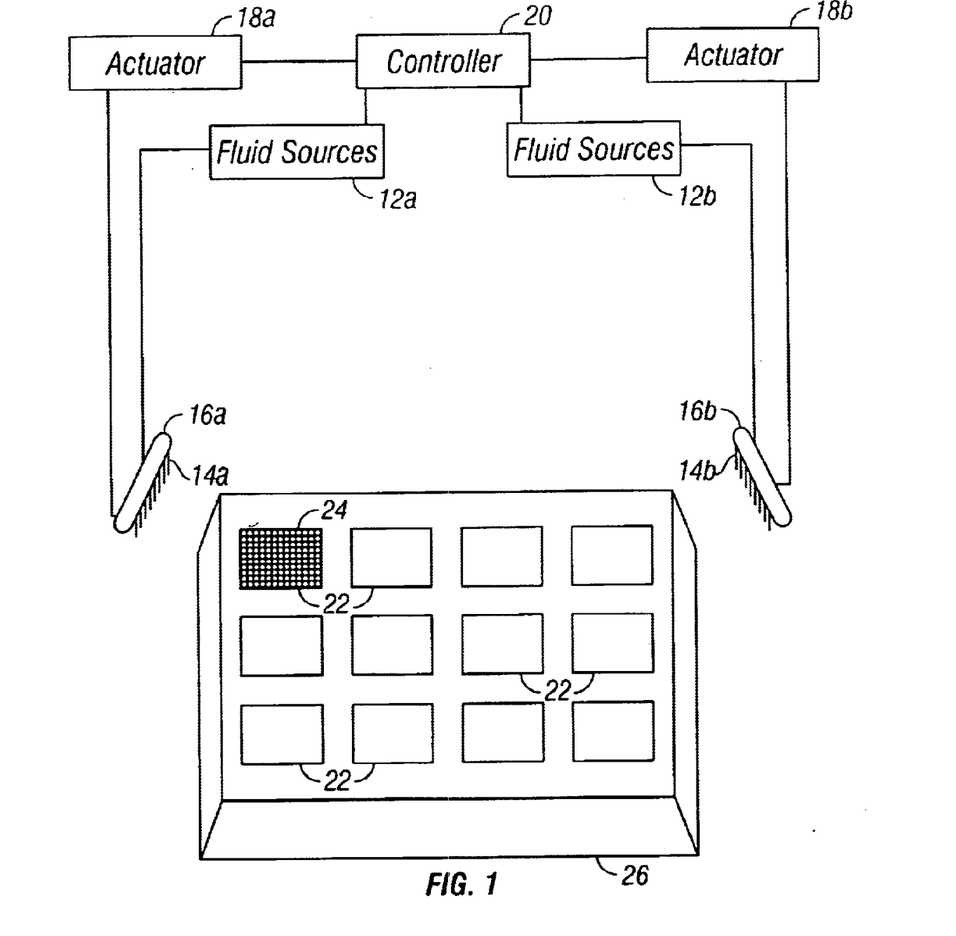
FIG. 1 is a simplified schematic diagram of a multi-channel reagent dispensing system in accordance with an embodiment of the present invention.

The supports 15a, 15b for the dispenser heads 14a, 14b are driven by the actuators 18a, 18b to pass over the cells 24, one cell per dispenser head at a time, and dispense into the cells various fluids including reagents, wash solvents, and the like.

The two sets of dispenser heads 14a, 14b may be passed over the cells 24 in different sequences and along different paths. The controller 20 is desirably a computer controller 20 which is programmed to move the dispenser head 14a, 14b in desirable sequences and along desirable paths to achieve the desired synthesis. The controller 20 may also be coupled with the reagent and wash solvent sources 16a, 16b to control the dispensing of the fluids through the dispenser heads 14a, 14b, for instance, by controlling operation of the valves 32a, 32b (FIGS. 2 and 3) between the sources 16a, 16b and the dispenser heads 14a, 14b, as described in more detail below.

In the embodiment shown, the two sets of dispenser heads 14a, 14b are fluidicly coupled to two different sets of reagent and wash solvent sources 12a, 12b. In other embodiments, there may be fewer or more sets of dispenser heads which are fluidicly coupled to the same or different sets of reagent and wash solvent sources. The reagent dispensing system 10 is desirably disposed or housed in an inert environment, such as nitrogen or argon.

Figure 2:
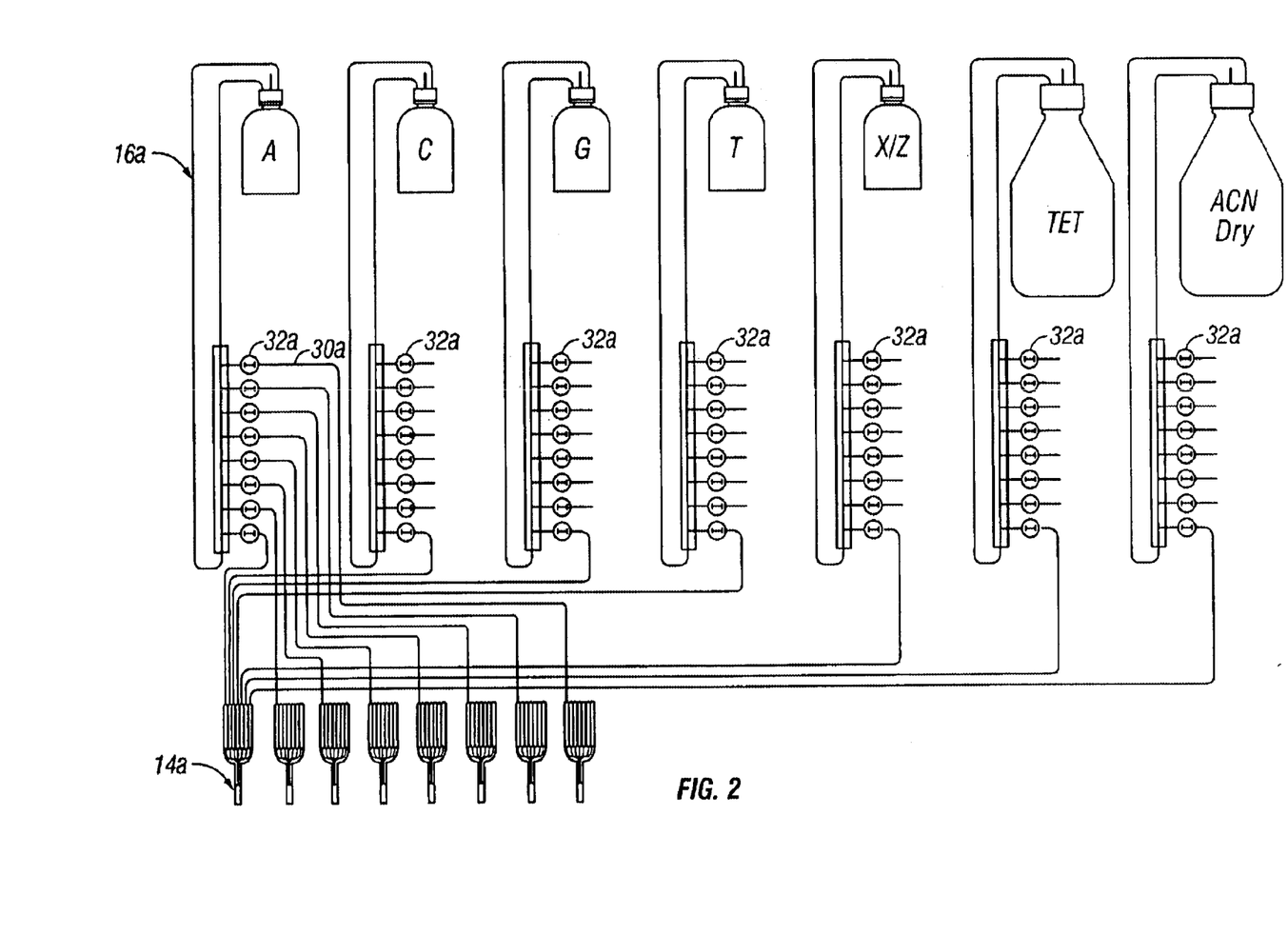
FIG. 2 is a schematic diagram of a first set of reagent dispenser heads in the reagent dispensing system of FIG. 1 according to an embodiment of the invention.
Figure 3:
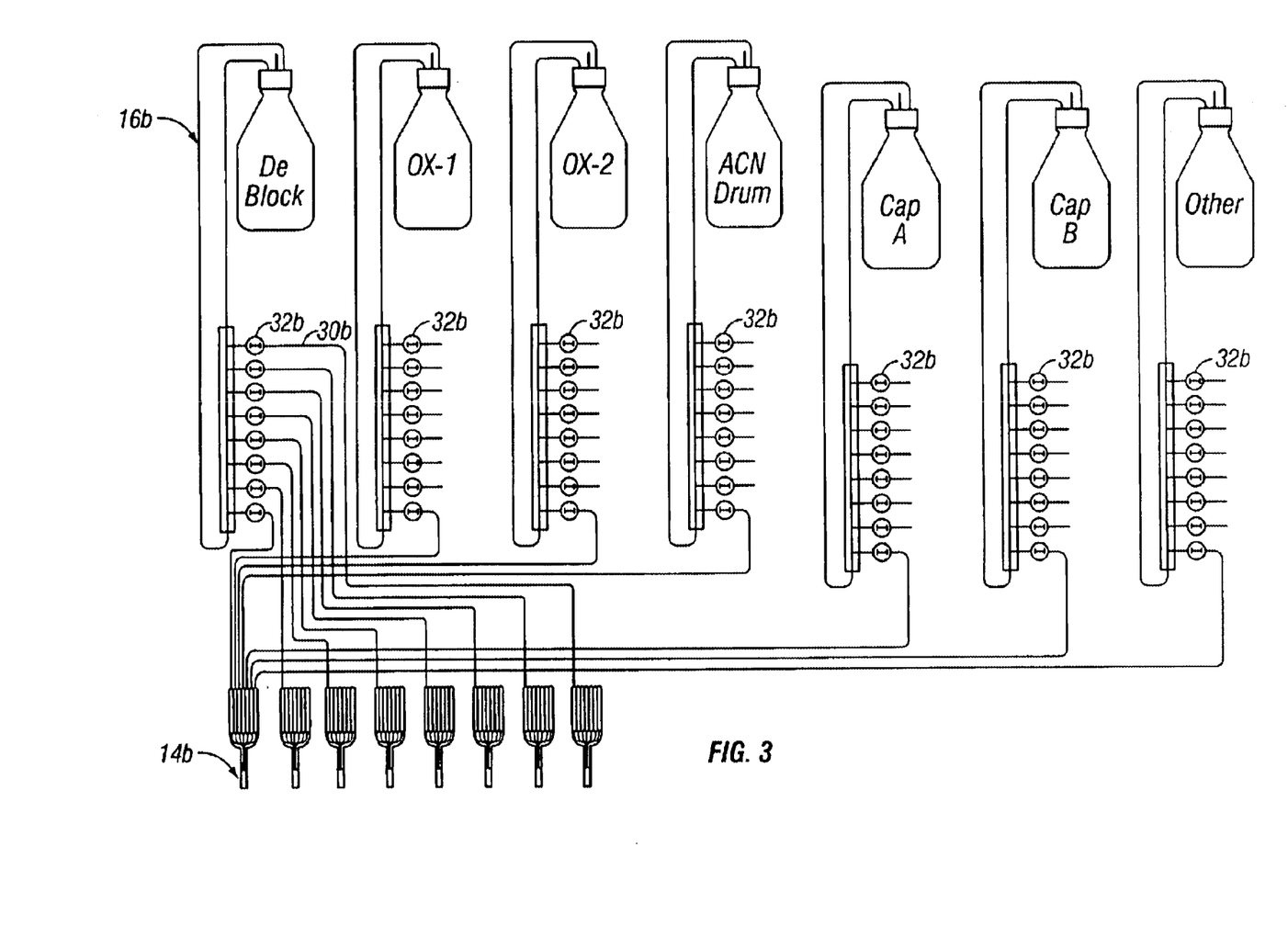
FIG. 3 is a schematic diagram of a second set of reagent dispenser heads in the reagent dispensing system of FIG. 1 according to an embodiment of the invention.

FIGS. 2 and 3 show an example of the two sets of dispenser heads 14a, 14b fluidicly coupled with two sets of reagents and wash solvent sources 16a, 16b. In FIG. 2, the first set of fluid sources 16a include bases A (adenine), C (cytosine), G (guanine), T (thymine), X/Z, TET (tetrazole), and ACN DRY (acetonitrile dry). The tetrazole may be replaced by another activator. The A, C, G, T, and X/Z are examples of building block elements, and may be replaced other building block elements from various molecule types in other embodiments. Solid phase polymer synthesis methods, for instance, utilize multiple addition of unit building blocks including other polynucleic acids (e.g., RNA or DNA/RNA hybrids), nucleic acid mimics (e.g., PNAs (peptide nucleic acids)), peptides, and oligosaccharides. The use of the system for combinatorial small molecule synthesis is also possible.

The sources 16a each include a plurality of fluid flow lines 30a for separately supplying fluids to each of the dispenser heads 14a. FIG. 2 shows eight channels represented by eight dispenser heads 14a each containing seven fluid lines 30a from the seven fluid sources 16a. For clarity, only one dispenser head is shown to receive fluid lines from all seven fluid sources 16a. Each fluid line 30a has a corresponding valve 32a that controls fluid flow from the corresponding fluid source 16a to the dispenser head 14a.

In FIG. 3, the second set of fluid sources 16b include DEBLOCK (acid deblock), OX-1 (oxidizer 1), OX-2 (oxidizer 2), ACN DRUM (acetonitrile drum), CAP A (capping agent A), CAP B (capping agent B), and OTHER. The sources 16a each include a plurality of fluid flow lines 30b for separately supplying fluids to each of the dispenser heads 14b. FIG. 2 shows eight dispenser heads 14b each containing seven fluid lines 30b from the seven fluid sources 16b. For clarity, only one dispenser head is shown to receive fluid lines from all seven fluid sources 16b. Each fluid line 30b has a corresponding valve 32b that controls fluid flow from the corresponding fluid source 16b to the dispenser head 14b.

Figure 4:
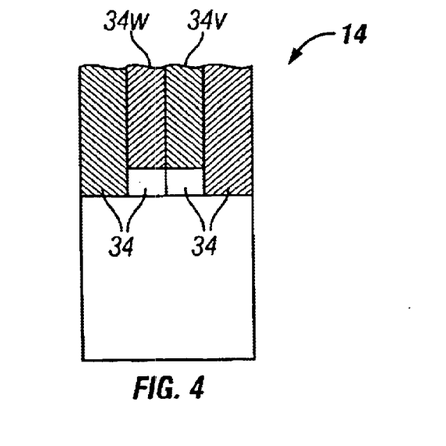
FIG. 4 is a sectional view of a reagent dispenser head according to an embodiment of the present invention.

The use of a separate, dedicated fluid line 30 (30a or 30b) between each fluid source 16 (16a or 16b) and each dispenser head 14 (14a or 14b) avoids the need for priming the lines, which saves time and reagents. The nozzles 34 (see FIG. 4) of the fluid lines 30 are clustered into the dispenser head 14 having an output size comparable to the size of the cells 24 for dispensing fluids into the cells 24. FIG. 4 shows a cluster of the fluid nozzles 34 in a dispenser head 14. In a specific embodiment, each cell 24 has a diameter of about 9 mm or less, and the dispensing end of each dispenser head 14 as a maximum dimension of about 9 mm. There are about eight nozzles 34 clustered in the dispensing head 14, each nozzle 34 having an outer diameter of less than about $1/16$ inch.

Because each dispenser head 14 has a nozzle 34 for the fluid line 30 from each fluid source 16 within the set, the set of dispenser heads 14 need only make one pass over the cells 24 to supply fluids from the entire set to the cells 24 in a particular dispensing sequence, thereby improving throughput. The opening and closing of the valves 32 (32a or 32b) are desirably automatically performed by computer control. For instance, the valves 32 may be operatively coupled with the controller 20 which is programmed to dispense fluids according to a desired synthesis procedure.

Each set of fluid sources 16 desirably includes a washing solvent such as acetonitrile. The wash solvent washes the dispenser heads 14 at various stages during the synthesis procedure to keep the heads 14 clean. The wash can also minimize or prevent cross-contamination between the openings of the fluid nozzles 34 clustered within each head 14. As shown in FIG. 4, the nozzle tip of the wash nozzle $34_W$ for dispensing acetonitrile or other wash solvents may be disposed slightly above or proximal of the tips of the remaining nozzles 34 to ensure that the other nozzles 34 are cleaned by the wash solvent dispensed through the wash nozzle $34_W$. In addition, a vacuum nozzle $34_V$ is desirably provided inside the dispenser head 14 to draw out residual fluids in the dispenser head 14 to minimize or eliminate cross-contamination. The tip of the vacuum nozzle $34_V$ is desirably disposed slight above or proximal of the tips of the reagent nozzles 34.

Figure 5:
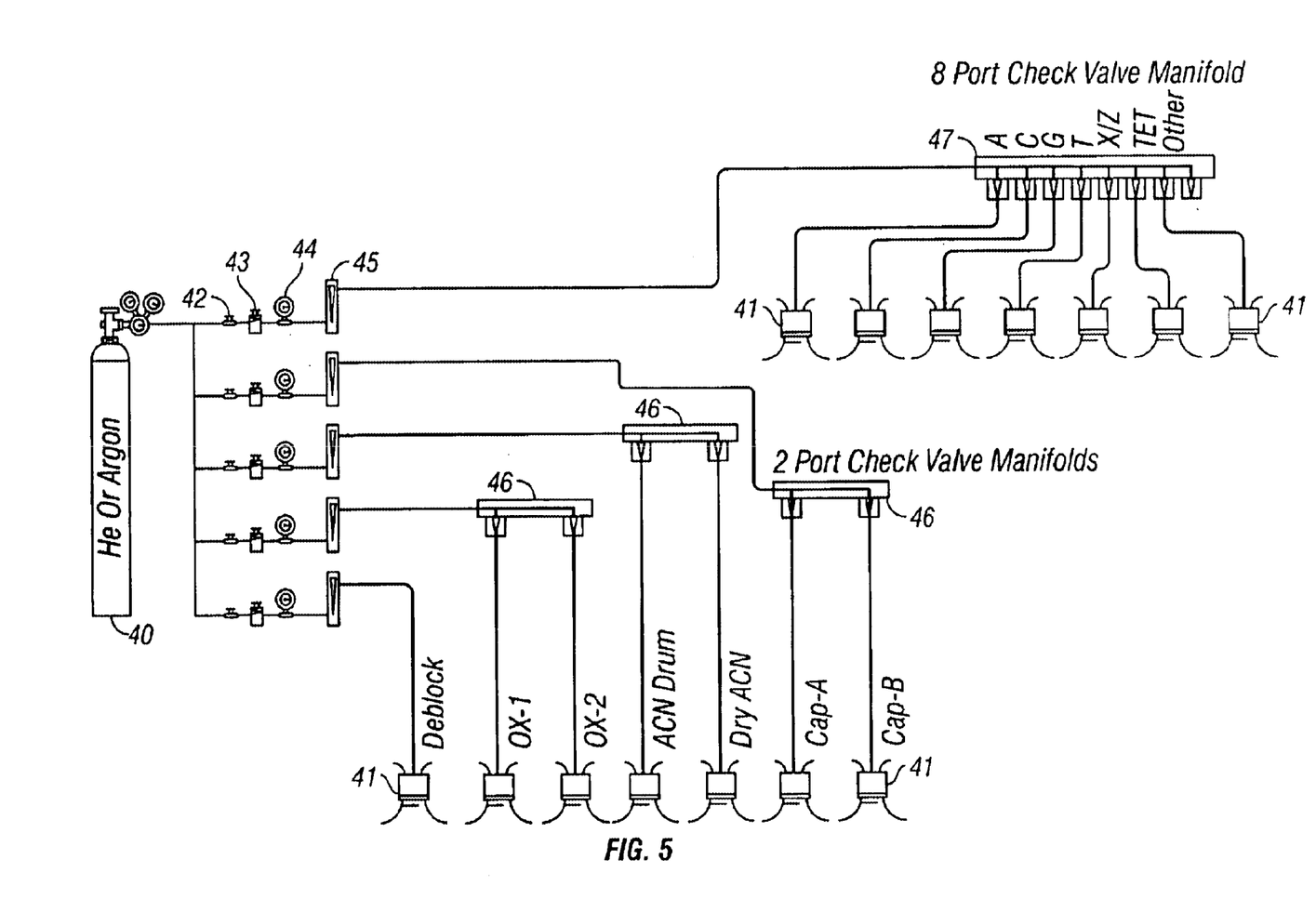
FIG. 5 is a schematic diagram of check valve manifolds for pressurizing the fluid sources in the multi-channel reagent dispensing system of FIG. 1.

The fluid sources 12 are provided in pressurized containers or bottles to drive the fluids through the fluid lines 30 to the dispenser heads 14 by the pressure differential. FIG. 5 shows a gas source 40 of inert gas such as helium (He) or argon (Ar) used to pressurize the fluid containers 41. The gas source 40 is coupled to a plurality of lines having a manual supply valve 42, a pressure regulator 43, a pressure meter 44, and a flow meter 45. For some containers 41, multiple-port check valve manifolds are used. FIG. 5 shows, for instance, several 2-port check valve manifolds 46 and an 8-port check valve manifold 47. Of course, other suitable pressure control and valve arrangements may be used. In other embodiments, pumps may be used to generate the fluid flow from the fluid sources to the dispenser heads.

There are numerous ways to dispense the desired amount of fluids from the sources 16 into the cells 24. In one embodiment, the flow from the source 16 to the cell 24 is generated by the pressure in the pressurized container for the source 16. The flow rate depends on the number of open valves 32 at that point in time. The larger the number of open valves 32, the lower the flow rate and the longer time it takes to keep the valve 32 open to dispense a given amount of fluid into the cell 24. The controller 20 is programmed to calculate the flow rate based on the number of open valves 32 and compute the time required to keep each valve 32 open to dispense the desired amount of fluid at that flow rate.

Figure 6:
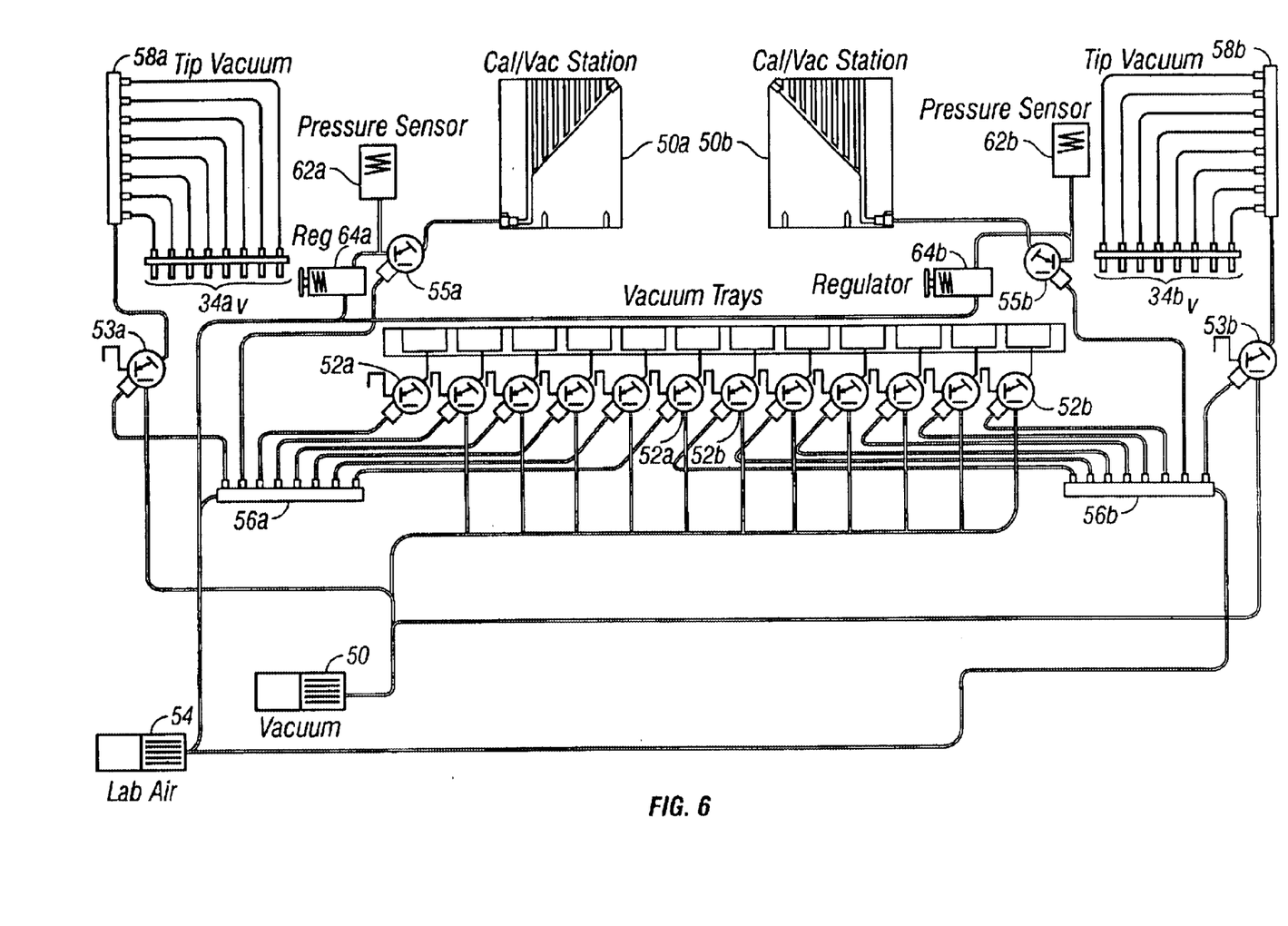
FIG. 6 is a schematic diagram of a vacuum system in the multi-channel reagent dispensing system of FIG. 1.

FIG. 6 shows the vacuum system in the multi-channel reagent dispensing system 10. A vacuum source 50 is coupled with the vacuum trays 22 (see FIG. 1) via vacuum valves 52 to draw the reagents through the reaction cells 24 disposed in the vacuum trays 22. A first set of vacuum valves 52a are provided for the six vacuum trays 22 on the left side of the body 26, and a second set of vacuum valves 52b are provided for the six vacuum trays 22 on the right side of the body 26, in FIG. 1 Any suitable valves may be used. In the embodiment shown, the vacuum valves 52a and 52b are pneumatic valves driven pneumatically by a pneumatic source 54 such as an air source or the like via air or gas manifolds 56a and 56b, respectively. An example of a suitable valve is a diaphragm-activated valve available from Parker of Tucson, Ariz. The vacuum source 50 is further coupled with the vacuum nozzles $34a_V$, $34b_V$ for removing residual reagents in the dispenser heads 14a, 14b (see FIG. 4), via a first (or left) vacuum valve 53a for the first set of dispenser heads 14a and a second (or right) vacuum valve 53b for the second set of dispenser head 14b. The valves 53a, 53b that are pneumatically driven by the pneumatic source 54. Vacuum manifolds 58a, 58b are provided for the two sets of vacuum nozzles $34a_V$, $34b_V$ in each set of dispenser heads 14a, 14b (see FIGS. 2 and 3).

The pneumatic source 54 further supplies a gas to a pair of CAL/VAC (calibration/vacuum) stations 60 associated with the two sets of dispenser heads 14a, 14b via vacuum valves 55a, 55b. The CAL/VAC stations 60 are used as waste stations for priming lines and rinsing nozzle tips, and may also be used to check the flow rates through the nozzle tips of the nozzles 34 for calibration. For each set of valves, a pressure sensor 62a or 62b is used to sense the pressure of the gas provided by the pneumatic source 54, and a pressure regulator 64a or 64b is used to regulate the pressure.

Figure 7A:
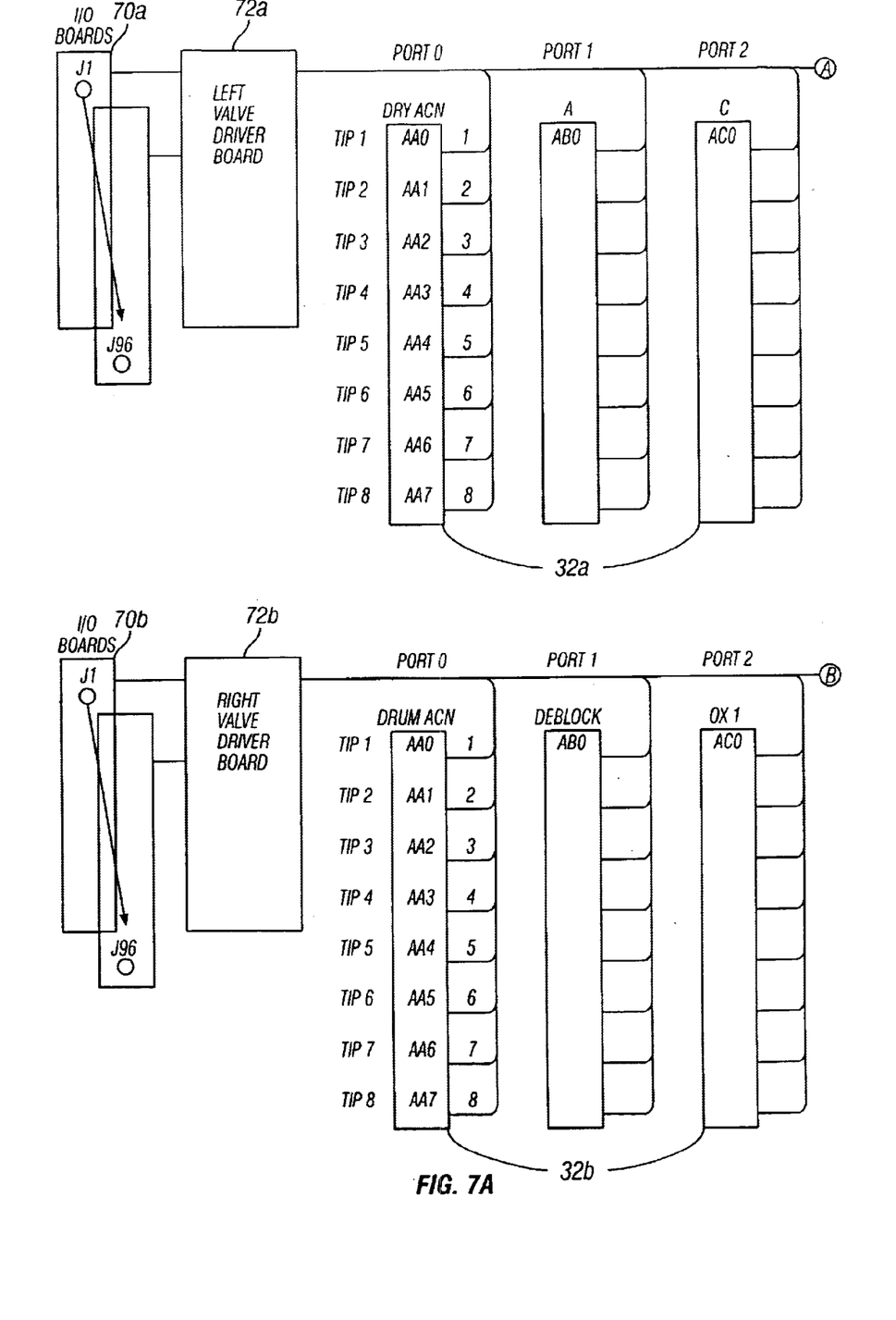
FIG. 7 is a schematic diagram of an interface between the controller and various valves in the multi-channel reagent dispensing system of FIG. 1.
Figure 7B:
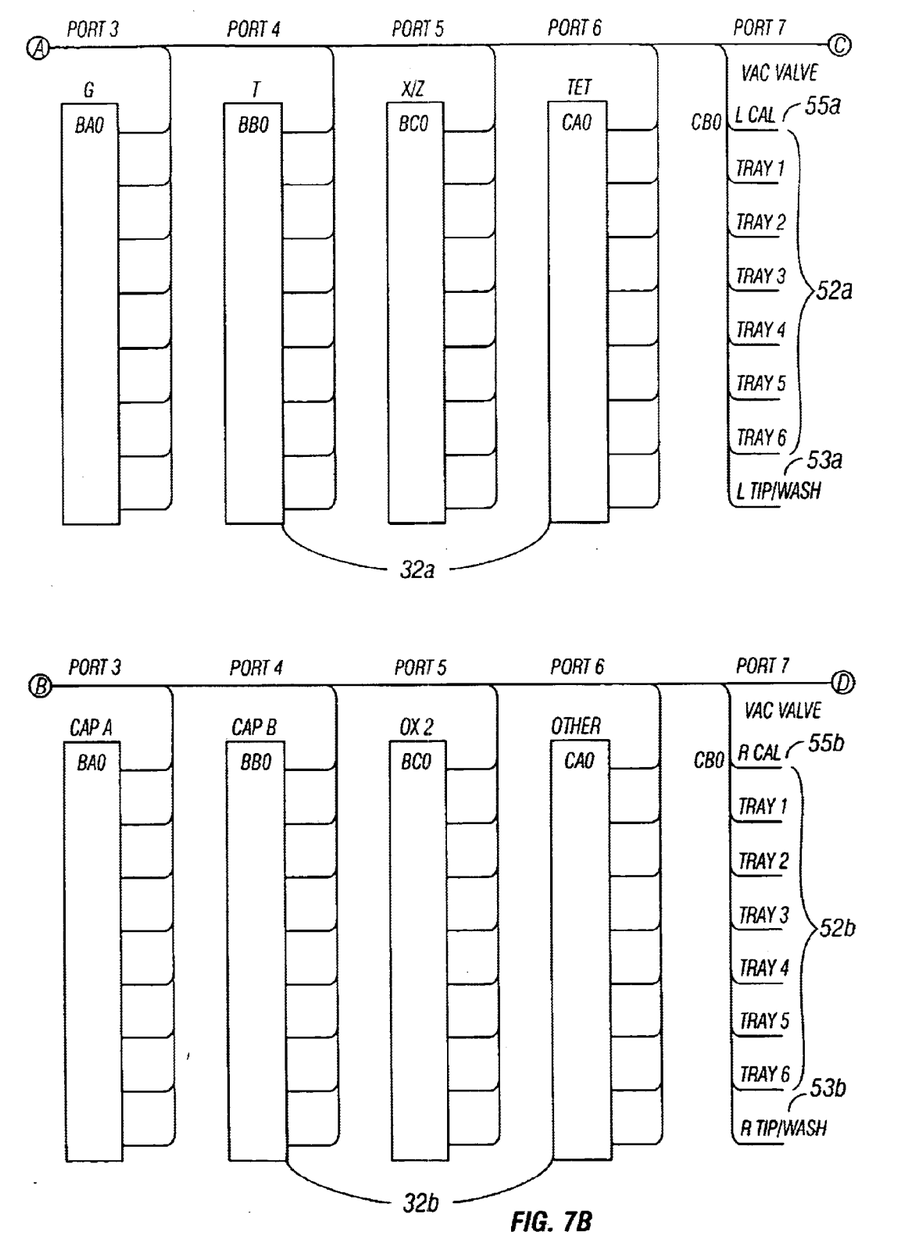
Figure 7C:
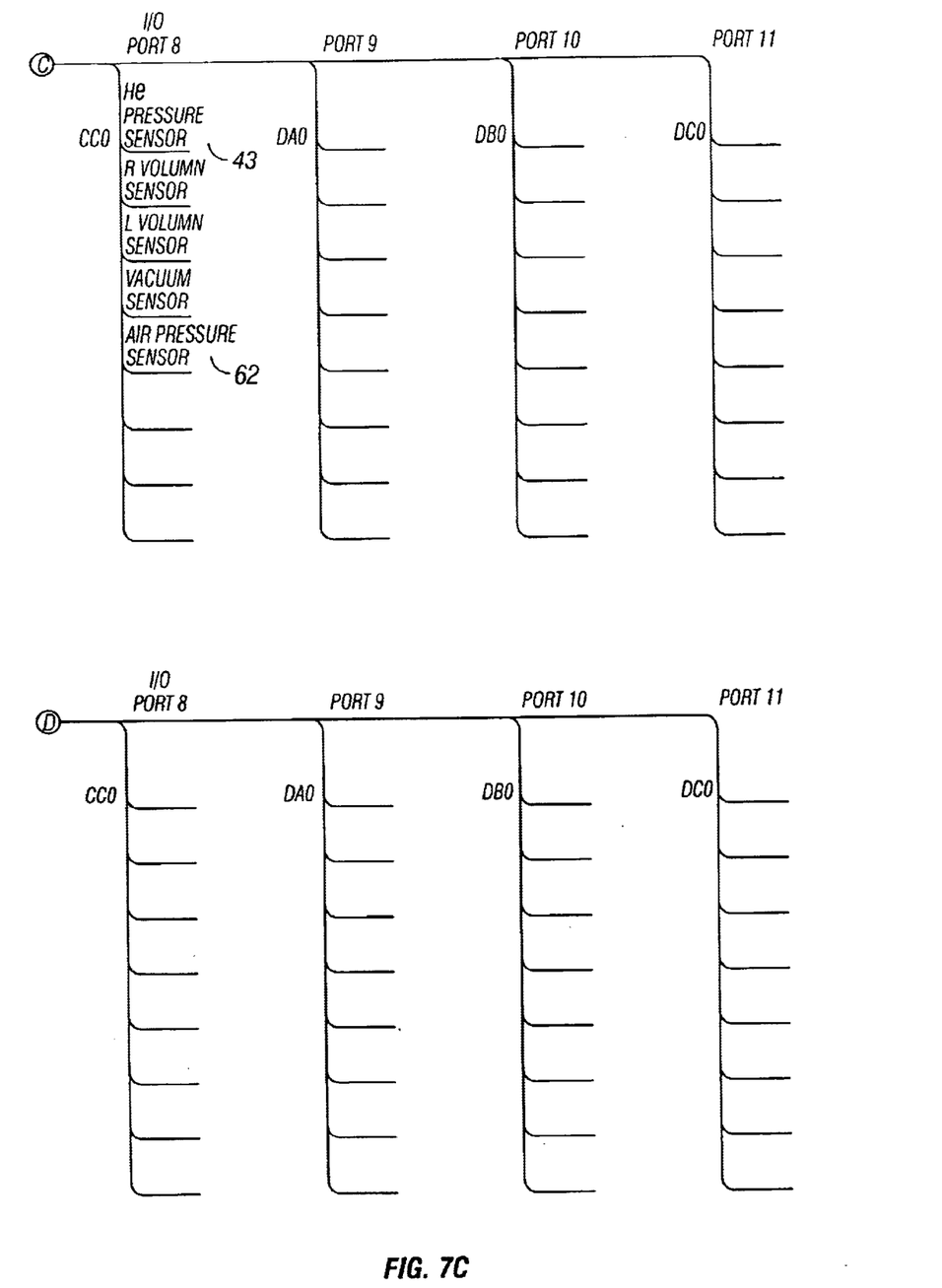

FIG. 7 shows the interface between the controller 20 and various valves in the multi-channel reagent dispensing system 10. First I/O boards 70a and a first or left valve driver board 72a are provided for interface with the valves for the first (or left) set of dispenser heads 14a. The valves include the dispenser head fluid line valves 32a for the seven fluid sources (DRY ACN, A, C, G, T, X/Z, TET) associated with the eight dispenser heads 14a. The seven fluid sources take up seven ports. An eighth port is used for vacuum valves, which include vacuum valves 52a (see FIG. 6) for the six vacuum trays 22 on the left side of the body 26 (see FIG. 1), the vacuum valve 53a for the first (or left) vacuum nozzles $34a_V$, and the vacuum valve 55a for the first (or left) CAL/VAC station 56a (see FIG. 6). Additional ports may be provided as shown in FIG. 7. For instance, one port (PORT 8) may provide the interface for the inert gas (e.g., He) pressure sensor 43 (see FIG. 5), air pressure sensor 62, and other vacuum or volume sensors or the like.

Likewise, first I/O boards 70b and a second or right valve driver board 72b are provided for interface with the valves for the second (or right) set of dispenser heads 14b. The valves include the dispenser head fluid line valves 32b for the seven fluid sources (DRUM ACN, DEBLOCK, OX-1, CAP A, CAP B, OX-2, OTHER) associated with the eight dispenser heads 14b. The seven fluid sources take up seven ports. An eighth port is used for vacuum valves, which include vacuum valves 52b (see FIG. 6) for the six vacuum trays 22 on the left side of the body 26 (see FIG. 1), the vacuum valve 53b for the second (or right) vacuum nozzles 34$b_V$, and the vacuum valve 55b for the second (or right) CAL/VAC station 56b (see FIG. 6). Additional ports may be provided as shown in FIG. 7.

In operation, the controller 20 controls the first actuator 18a to move the first set of dispenser heads 14a across the reaction cells 24 in each vacuum tray 22 of FIG. 1. The first actuator 18a aligns the first dispenser heads 14a with the cells 24 for dispensing reagents from the first set of reagent and wash solvent sources 12a into the cells 24 simultaneously. The type and amount of reagents dispensed, as well as the delivery of a wash solvent such as acetonitrile, are controlled by the opening and closing of the dispenser head fluid line valves 32a by the controller 20 (see FIG. 7). Typically, one reagent or wash solvent is dispensed at a time. The controller 20 further controls the vacuum valve 53a for the vacuum nozzles 34$a_V$ to remove residual reagents from the dispenser heads 14a and prevent cross-contamination between different reagents in the dispenser heads 14a (see FIG. 6). The controller 20 also controls the vacuum valve 55a for calibration at the CAL/VAC station 50a (see FIG. 6), and the vacuum valve 52 associated with the particular vacuum tray 22 in which the reaction cells 24 are disposed to receive the reagents during that time. The first actuator 18a drives the dispenser heads 14a across the reaction cells 24 in sequence to dispense the reagents according to desired protocols as programmed into the controller 20 to achieve the desired synthesis steps in each of the cells 24.

The other synthesis steps involve dispensing fluids from the second set of reagent and wash solvent sources 12b into the reaction cells 24. The controller 20 controls the second actuator 18b to move the second set of dispenser heads 14b across the reaction cells 24 in each vacuum tray 22 of FIG. 1. The second actuator 18b aligns the second dispenser heads 14b with the cells 24 for dispensing reagents from the second set of reagent and wash solvent sources 12b into the cells 24 simultaneously. The type and amount of reagents dispensed, as well as the delivery of a wash solvent such as acetonitrile, are controlled by the opening and closing of the dispenser head fluid line valves 32b by the controller 20 (see FIG. 7). Typically, one reagent or wash solvent is dispensed at a time. The controller 20 further controls the vacuum valve 53b for the vacuum nozzles 34$b_V$ to remove residual reagents from the dispenser heads 14b and prevent cross-contamination between different reagents in the dispenser heads 14b (see FIG. 6). The controller 20 also controls the vacuum valve 55b for calibration at the CAL/VAC station 50b (see FIG. 6), and the vacuum valve 52 associated with the particular vacuum tray 22 in which the reaction cells 24 are disposed to receive the reagents during that time. The second actuator 18b drives the dispenser heads 14b across the reaction cells 24 in sequence to dispense the reagents according to desired protocols as programmed into the controller 20 to achieve the desired synthesis steps in each of the cells 24.

The two actuators 18a, 18b may be controlled to move the dispenser heads 14a, 14b to different vacuum trays 22 for dispensing fluids into different cells 24 at different locations in any desirable sequence. For example, the second dispenser heads 14b may follow the path of the first dispenser heads 14a, but may also take on a different path, such as a staggered formation with respect to the first dispenser heads 14a. Because each set of dispenser heads 14a, 14b can dispense fluids simultaneously from a plurality of fluid sources, delivery of reagents and wash solvents into multiple cells can be achieve without excessive movements and elaborate control and positioning of the dispenser heads, thereby improving throughput and reducing the complexity of the delivery procedure.

The above-described arrangements of apparatus and methods are merely illustrative of applications of the principles of this invention and many other embodiments and modifications may be made without departing from the spirit and scope of the invention as defined in the claims. For instance, instead of individual reaction columns placed within the vacuum tray, the reaction sites may be formed on a single block and placed in the vacuum tray. The cross-section of the reaction sites may be round, square, or of other shapes. In addition, the cells 24 may each have a diameter greater than 9 mm in some embodiments. In general, the size of the dispensing end of each dispenser head 14 is smaller than the size of the cell 24 receiving fluid from the dispenser head 14. For a standard 96 well microtiter plate, the size is 9 mm. In another system there may be 20 lines in the nozzle bundle within a single dispenser head, and the size of the dispensing end of the dispenser head will be about 12 mm. The reactor cell will have an orifice of about 14 mm and there will be 48 reactor cells per microtiter plate. The scope of the invention should, therefore, be determined not with reference to the above description, but instead should be determined with reference to the appended claims along with their full scope of equivalents.

What is claimed is:

1. A multi-channel reagent dispenser head for introducing a plurality of reagents into a reaction cell, the dispenser head comprising:

a dispenser head body having a dispensing end which is configured to dispense a plurality of reagents from a plurality of reagent sources; and a group of nozzles including a plurality of reagent dispensing nozzles which are fluidicly coupled with the plurality of reagent sources, the group of nozzles being clustered to provide a plurality of nozzle outlets in the dispenser head body to be positioned simultaneously at the reaction cell and introduce one or more reagents from the plurality of reagent sources through the dispensing end of the dispenser head body into the reaction cell, wherein the group of nozzles include a vacuum nozzle which is coupled to a vacuum source.

2. The dispenser head of claim 1 wherein the nozzle outlet of the vacuum nozzle is disposed proximal of the nozzle outlets of the reagent dispensing nozzles.

3. The dispenser head of claim 1 wherein the dispensing end of the dispenser head body has a maximum dimension of about 9 mm.

4. The dispenser head of claim 1 wherein the nozzles each have an outer diameter of less than about 1/16 inch.

5. The dispenser head of claim 1 wherein the group of nozzles include a wash nozzle which is fluidicly coupled with a source of wash solvent.

6. The dispenser head of claim 5 wherein the wash solvent comprises acetonitrile.

7. The dispenser head of claim 1 wherein the plurality of reagent dispensing nozzles are each separately coupled with one of the plurality of reagent sources.

8. The dispenser head of claim 7 wherein the plurality of reagent dispensing nozzles are separately coupled with reagent sources of bases A, C, G, T, and an activator.

9. The dispenser head of claim 7 wherein the plurality of reagent dispensing nozzles are separately coupled with reagent sources of acid deblock, oxidizers, and capping agents.

10. A multi-channel reagent dispenser apparatus for introducing a plurality of reagents into a plurality of reaction cells, the apparatus comprising:

a plurality of reagent sources;

a plurality of reagent dispensing nozzles each coupled with one of the plurality of reagent sources;

a plurality of dispenser heads, each dispenser head including a dispenser head body having a dispensing end which is configured to dispense a plurality of reagents from the plurality of reagent sources, each dispenser head body having therein a group of nozzles being clustered to provide a plurality of nozzle outlets in the dispenser head body to be positioned simultaneously at one of the reaction cells and introduce one or more reagents from the plurality of reagent sources through the dispensing end of the dispenser head body into the reaction cell, the group of nozzles including more than one reagent dispensing nozzle from the plurality of reagent dispensing nozzles.

11. The apparatus of claim 10 comprising a plurality of reagent dispensing nozzle valves each coupled with one of the reagent dispensing nozzles to control reagent flow from the reagent sources to the reagent dispensing nozzles.

12. The apparatus of claim 10 wherein the plurality of reagent sources each are delivered to the reagent dispensing nozzles by pressurization with an inert gas.

13. The apparatus of claim 10 wherein the reaction cells are evacuated under vacuum assist.

14. The apparatus of claim 10 wherein the reaction cells are disposed in an array provided in a plurality of vacuum trays which are formed on a single block.

15. The apparatus of claim 10 wherein the apparatus is disposed in an inert environment.

16. The apparatus of claim 10 further comprising at least one source of wash solvent and at least one wash nozzle coupled with the at least one source of wash solvent, wherein the group of nozzles clustered in each dispenser head body include at least one wash nozzle.

17. The apparatus of claim 16 further comprising at least one wash nozzle valve each coupled with one of the at least one wash nozzle to control wash solvent flow from the at least one source of wash solvent to the at least one wash nozzle.

18. The apparatus of claim 10 wherein the group of nozzles clustered in each dispenser head body include a vacuum nozzle which is coupled to a vacuum source.

19. The apparatus of claim 18 further comprising a vacuum nozzle valve coupled with the vacuum nozzle to control vacuum flow through the vacuum nozzle.

20. The apparatus of claim 10 wherein the plurality of dispenser heads comprise at least one first dispenser head and at least one second dispenser head, each first dispenser head having therein a cluster of first nozzles being coupled with a first set of the plurality of reagent sources, each second dispenser head having therein a cluster of second nozzles being coupled with a second set of the plurality of reagent sources which are different from the first set of reagent sources.

21. The apparatus of claim 20 wherein the first set of reagent sources comprise bases A, C, G, T, and an activator.

22. The apparatus of claim 20 wherein the second set of reagent sources comprise acid deblock, oxidizers, and capping agents.

23. The apparatus of claim 20 wherein the dispensing end of each dispenser head body has a maximum dimension of about 9 mm.

24. The apparatus of claim 23 wherein the plurality of dispenser heads comprise a plurality of first dispenser heads and a plurality of second dispenser heads, wherein the first dispenser heads are spaced about 9 mm apart, and wherein the second dispenser heads are spaced about 9 mm apart.

25. The apparatus of claim 20 further comprising a first actuator configured to move each of the at least one first dispenser head from one reaction cell to another reaction cell to introduce reagents from the first set of reagent sources into the reaction cells.

26. The apparatus of claim 25 further comprising a second actuator configured to move each of the at least one second dispenser head from one reaction cell to another reaction cell to introduce reagents from the second set of reagent sources into the reaction cells.

27. The apparatus of claim 26 further comprising a controller coupled with the first and second actuators to automatically control movements of the at least one first dispenser head and the at least one second dispenser head to introduce reagents from the first and second sets of reagent sources separately into the reaction cells.

28. The apparatus of claim 27 further comprising a plurality of reagent dispensing nozzle valves each coupled with one of the reagent dispensing nozzles, wherein the controller is coupled with the reagent dispensing nozzle valves to control reagent flow from the reagent sources to the first nozzles in the at least one first dispenser head and to the second nozzles in the at least one second dispenser head.

* * * * *